(12) United States Patent
Datta et al.

(10) Patent No.: US 11,864,941 B2
(45) Date of Patent: Jan. 9, 2024

(54) SYSTEM AND METHOD FOR COLLIMATOR SCREENING IN A COMPUTED TOMOGRAPHY SYSTEM

(71) Applicant: GE PRECISION HEALTHCARE LLC, Wauwatosa, WI (US)

(72) Inventors: Arka Datta, Waukegan, IL (US); John Moore Boudry, Waukesha, WI (US); Brandon Allan Smith, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 146 days.

(21) Appl. No.: 17/493,005

(22) Filed: Oct. 4, 2021

(65) Prior Publication Data

US 2023/0109837 A1     Apr. 13, 2023

(51) Int. Cl.
*A61B 6/00* (2006.01)
*A61B 6/03* (2006.01)
*A61B 6/06* (2006.01)

(52) U.S. Cl.
CPC ............... *A61B 6/582* (2013.01); *A61B 6/03* (2013.01); *A61B 6/06* (2013.01)

(58) Field of Classification Search
None
See application file for complete search history.

(56) References Cited

U.S. PATENT DOCUMENTS

| 5,644,614 A | 7/1997 | Toth et al. |
| 6,141,402 A | 10/2000 | Toth |
| 7,257,187 B2 | 8/2007 | Chao et al. |
| 9,693,747 B2 | 7/2017 | Laor et al. |
| 2017/0209106 A1 * | 7/2017 | Ikhlef ..................... A61B 6/06 |

FOREIGN PATENT DOCUMENTS

| CN | 109770935 A | 5/2019 |
| EP | 1065670 | 1/2001 |

OTHER PUBLICATIONS

EP Application 22196735.9 Extended Search Report dated Feb. 10, 2023, 2 pgs.

* cited by examiner

*Primary Examiner* — Dani Fox
(74) *Attorney, Agent, or Firm* — Fletcher Yoder P.C.

(57) ABSTRACT

A method for verifying aperture positions of a pre-patient collimator of a computed tomography (CT) imaging system includes obtaining data collected by an X-ray measurement device having detector elements subjected to X-rays emitted from an X-ray source of the CT imaging system with the pre-patient collimator at an expected aperture position. The method also includes calculating a measured collimator aperture position for the pre-patient collimator based on the obtained data. The method further includes comparing the measured collimator aperture position to a system specification for the expected aperture position for the CT imaging system. The method even further includes generating an output based on the comparison of the measured collimator aperture position to the system specification.

20 Claims, 6 Drawing Sheets

SYSTEM AND METHOD FOR COLLIMATOR SCREENING IN A COMPUTED TOMOGRAPHY SYSTEM

BACKGROUND

The subject matter disclosed herein relates to medical imaging systems and, more particularly, to collimator screening.

In computed tomography (CT), X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT systems a detector array, including a series of detector elements or sensors, produces similar signals through various positions as a gantry is displaced around a patient, allowing volumetric reconstructions to be obtained.

A CT imaging system may include a pre-patient collimator to ensure the subject of interest receives the intended dose. The collimator blades of the pre-patient collimator are adjusted in front of the X-ray source to create an appropriate opening or aperture to transmit X-rays for the scan as set by the operator. It is important that the collimator blades are correctly and precisely opened to the intended aperture as a minor mispositioning may lead to a substantial dose mismatch to the subject of interest.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a method for verifying aperture positions of a pre-patient collimator of a computed tomography (CT) imaging system is provided. The method includes obtaining data collected by an X-ray measurement device having detector elements subjected to X-rays emitted from an X-ray source of the CT imaging system with the pre-patient collimator at an expected aperture position. The method also includes calculating a measured collimator aperture position for the pre-patient collimator based on the obtained data. The method further includes comparing the measured collimator aperture position to a system specification for the expected aperture position for the CT imaging system. The method even further includes generating an output based on the comparison of the measured collimator aperture position to the system specification.

In another embodiment, a method for verifying aperture positions of a pre-patient collimator of a CT imaging system including an X-ray source and a radiation detector is provided. The method includes acquiring air scan data by causing X-rays to be emitted from the X-ray source toward the radiation detector with the pre-patient collimator at different expected aperture positions. The method also includes calculating respective widths of respective normalized intensity distribution profiles for the pre-patient collimator at the different expected aperture positions based on the obtained air scan data. The method further includes converting the respective widths to respective doses utilizing a transfer function. The method includes determining a respective dose error estimate at the different expected aperture positions based on the respective doses. The method even further includes comparing the respective dose error estimates to respective dose tolerance thresholds for the different expected aperture positions. The method still further includes generating an output based on the comparison of the respective dose error estimates to the respective dose tolerance thresholds.

In a further embodiment, a CT imaging system is provided. The system includes an X-ray source configured to emit X-rays during operation. The system also includes a radiation detector configured to receive the X-rays. The system further includes a pre-patient collimator disposed between the X-ray source and the radiation detector and configured to shape a beam of the X-rays via an aperture. The system even further includes processing circuitry configured to perform acts. The acts include acquiring air scan data by causing X-rays to be emitted from the X-ray source toward the radiation detector with the pre-patient collimator at different expected aperture positions. The acts also include calculating respective widths of respective normalized intensity distribution profiles for the pre-patient collimator at the different expected aperture positions based on the obtained air scan data. The acts further include converting the respective widths to respective doses utilizing a transfer function. The acts include determining a respective dose error estimate at the different expected aperture positions based on the respective doses. The acts even further include comparing the respective dose error estimates to respective dose tolerance thresholds for the different expected aperture positions. The acts still further include generating an output based on the comparison of the respective dose error estimates to the respective dose tolerance thresholds.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context or image processing field utilizing a collimator to control a size of X-ray beams.

The present disclosure provides systems and methods for performing collimator screening in a CT imaging system. In particular, the systems and methods enable the verification of aperture positions of a pre-patient collimator. The disclosed embodiments include obtaining data (e.g., air scan data or calibration), via air scans, at different aperture positions for the pre-patient collimator. The data may be obtained by a detector of the CT imaging system or another X-ray measurement device separate from or independent of the CT imaging system. From the obtained data, measured collimator aperture positions may be determined for the different expected (e.g., intended or predetermined) aperture positions or settings. The measured aperture positions may be compared to the system specification for the CT imaging system to determine if any of the measured (i.e., actual) aperture positions are off from the expected aperture positions. In certain embodiments, normalized intensity distribution profiles may be calculated from the obtained data. A width of the normalized distribution profile (which serves as a measure of aperture position) may be converted to a dose which may be compared to an expected dose for an expected aperture position to determine a dose error estimate. The dose error estimate may then be compared to a dose tolerance threshold for the expected aperture position. The analysis of the aperture positions may be reported to the user and/or stored.

The disclosed embodiments provide a safety check to ensure collimator blades are correctly positioned. In addition, the disclosed embodiments may be utilized as a stand-alone tool or integrated with the daily refresh calibration process to enable the validation of the functionality of the collimator blades routinely. In certain embodiments, the parameters (i.e., analysis of the aperture positions) may be monitored remotely (for connected CT imaging systems) for preventive maintenance of the collimator. The disclosed embodiments provide a holistic approach combining system hardware and software for computation and analysis to corroborate the functionality of a critical hardware component (i.e., the pre-patient collimator) used in the CT imaging system to avoid providing an excessive radiation dose to a patient if the pre-patient collimator malfunctions (e.g., has an aperture opening larger than an expected aperture opening).

Figure 1:
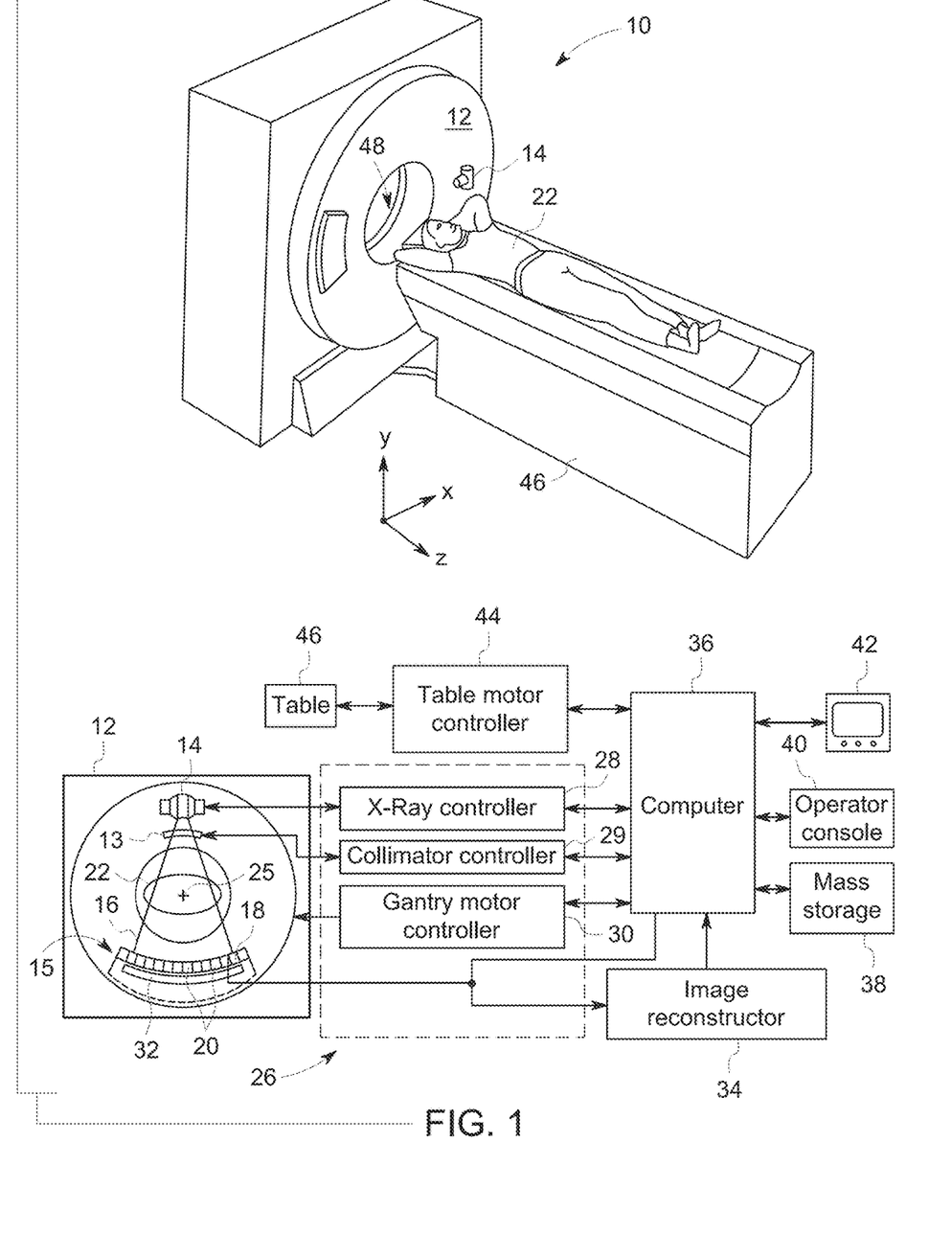
FIG. 1 is a combined pictorial view and block diagram of a computed tomography (CT) imaging system as discussed herein.

With the preceding in mind and referring to FIG. 1, a CT imaging system 10 is shown, by way of example. The CT imaging system includes a gantry 12. The gantry 12 has an X-ray source 14 that projects a beam of X-rays 16 toward a detector assembly 15 on the opposite side of the gantry 12. The X-ray source 14 projects the beam of X-rays 16 through a pre-patient collimator or collimator assembly 13 that determines the size of the beam of X-rays 16. The detector assembly 15 includes a collimator assembly 18 (post-patient collimator assembly), a plurality of detector modules 20 (e.g., detector elements or sensors), and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 25 (e.g., isocenter) so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to an X-ray source 14, a collimator controller 29 that controls a width of an aperture of the pre-patient collimator 13 (and, thus, the size of the beam of X-rays 16), and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 to position patient 22 and gantry 12. Particularly, table 46 moves portions of patient 22 through a gantry opening or bore 48.

Figure 2:
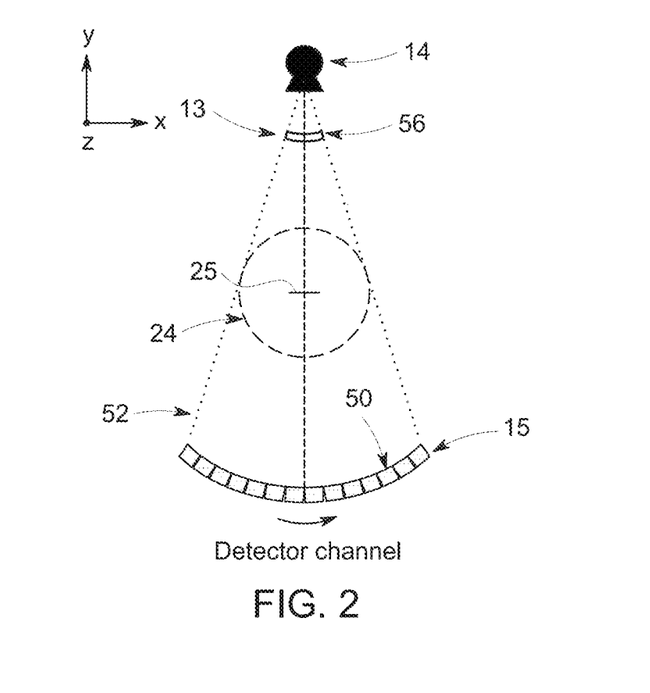
FIG. 2 is a schematic view of an X-ray source and a multi-row X-ray detector (e.g., as viewed in an X-Y plane), in accordance with aspects of the present disclosure.
Figure 3:
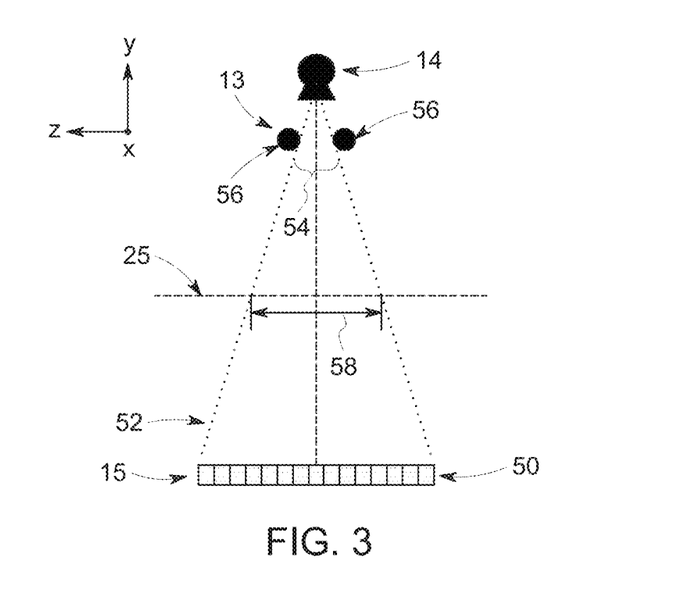
FIG. 3 is a schematic view of the X-ray source and the multi-row X-ray detector (e.g., as viewed in the Y-Z plane), in accordance with aspects of the present disclosure.

With the preceding discussion of an overall imaging system 10 in mind, and turning to FIGS. 2 and 3, an example of the X-ray source 14 and the detector assembly 15 (e.g., an X-ray detector having a plurality of rows 50) are illustrated in an X-Y plane (FIG. 2) and a Y-Z plane (FIG. 3), respectively. For convenience of explanation, the rotating gantry 12 with X-ray source 14 is rotated from the location shown in FIG. 1 to the top of 'the gantry (+Y direction). As depicted, the pre-patient collimator 13 is disposed between the X-ray source 14 and the detector assembly 15 and determines the shape of the X-ray beam 52. In particular, an opening or aperture 54 between a pair of collimator blades 56 of the pre-patient collimator 13 (as depicted in FIG. 3) shapes the X-ray beam 52. The field of view 24 and a beam width 58 corresponding to the size of the X-ray beam 52 intended for patient scanning are also illustrated. The correct positioning of the collimator blades 56 is important in ensuring that the patient receives the correct radiation dose and the correct area is scanned. The shape of the blades 56 are shown in different orientations in FIGS. 2 and 3. By way of example, the blades 56 are generally curved in the XY plane, with a circular leading edge in the YZ plane that determines the beam size. There are many other possible shapes of the blades in the XY plane including flat and angled; shapes of the leading edge in the YZ plane may also be rectangular or triangular, for example.

Figure 4:
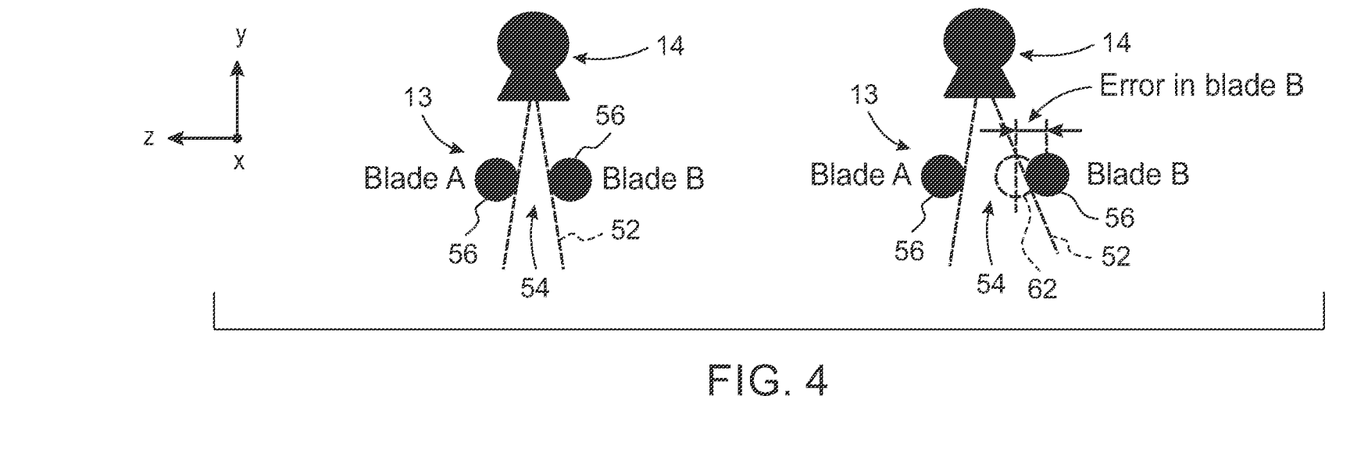
FIG. 4 is schematic view of collimator blades of a collimator with both blades correctly positioned (left side) and one of the collimator blades incorrectly positioned (right side), in accordance with aspects of the present disclosure.
Figure 5:
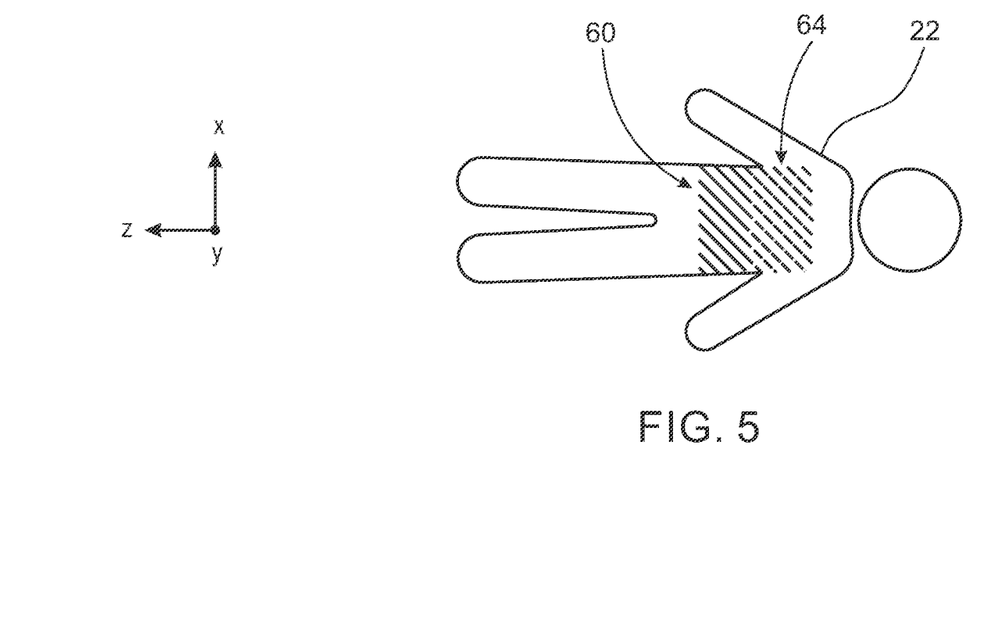
FIG. 5 is a schematic view of how collimator blade positioning affects the scanning area of a patient, in accordance with aspects of the present disclosure.

FIG. 4 is schematic view of the collimator blades 56 of the pre-patient collimator 13 with both blades 56 (e.g., blades A and B) correctly positioned (left side) and one of the collimator blades 56 (blade B) incorrectly positioned (right side). As depicted in FIG. 5 the correct positioning of the collimator blades 56 (as seen on the left side of FIG. 4) results in the correct and desired area 60 (shown in solid lines) of the patient 22 being scanned. As depicted on the right side of FIG. 4, blade B is incorrectly positioned relative to a desired or correct position 62. The incorrect positioning of blade B as shown on the right side of FIG. 4 results in an incorrect and undesired area 64 (shown in dashed lines) of the patient 22 being scanned (as depicted in FIG. 5). As disclosed herein, systems and methods are provided for checking or validating the positioning of the collimator blades 56 of the pre-patient collimator to ensure patients 22 receive the proper dose and the correct areas are scanned.

Figure 6:
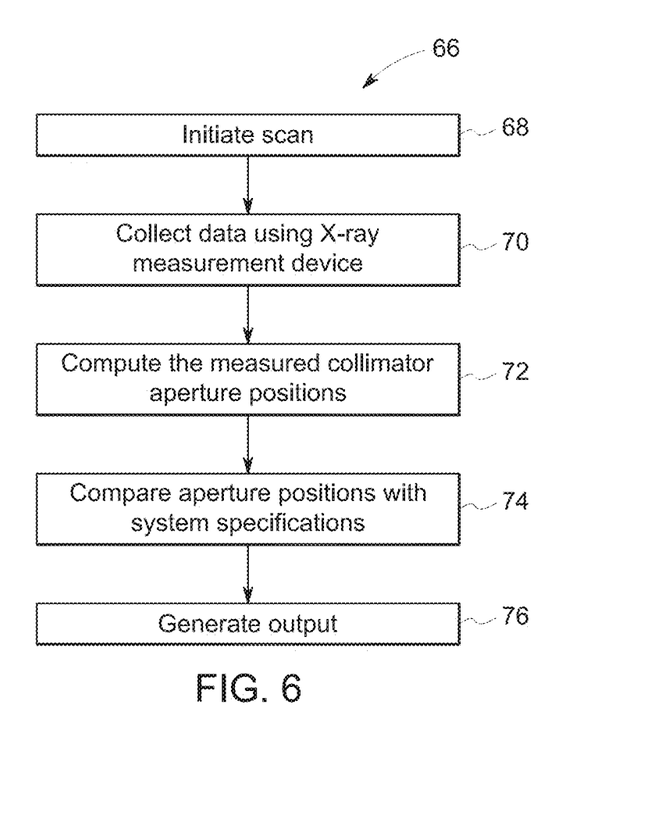
FIG. 6 is a flow chart of a method for verifying aperture positions of a pre-patient collimator (e.g., of the CT imaging system in FIG. 1), in accordance with aspects of the present disclosure.

FIG. 6 is a flow chart of a method 66 for verifying aperture positions of a pre-patient collimator (e.g., of the CT imaging system in FIG. 1). One or more steps of the method 66 may be performed by one or more components (e.g., processing circuitry) of the CT imaging system in FIG. 1 or a device separate or remote from the CT imaging system. The method 66 includes initiating calibration scans or air scans (e.g., scans with no object within the bore of the gantry) on the CT imaging system at different expected (e.g., intended or predetermined) aperture positions or settings (e.g., 5 millimeters (mm), 10 mm, etc.) for the pre-patient collimator (block 68).

The method 66 also includes collecting or obtaining data (e.g., calibration scan data or air scan data) using an X-ray measurement device having detector elements (block 70). In certain embodiments, the X-ray measurement device is the detector assembly of the CT imaging system. In other embodiments, the X-ray measurement device may be a device separate from or independent of the CT imaging system. Some examples of separate X-ray measurement devices include analog methods such as X-ray photo-sensitive films or digital methods such as a CCD camera coupled to an X-ray scintillator. The separate X-ray device may be able to determine a measure of spatial resolution (e.g., full width at half maximum).

The method 66 further includes computing or calculating the measured collimator aperture positions based on the obtained data at each of the different expected aperture positions (block 72). In certain embodiments (e.g., when the data is obtained via the detector assembly of the CT imaging system), the obtained data may be processed (e.g., normalized, bad pixel data removed, etc.) to determine a respective normalized intensity distribution profile at the different expected aperture positions from which the measured collimator aperture positions (e.g., a width of the respective normalized intensity distribution profile) may be obtained. These calculations (and subsequent calculations) may occur within the software of the CT imaging system. In certain embodiments (e.g., when the data is obtained via a separate or external X-ray measurement device), the calculations may occur on software of devices separate from the CT imaging system (e.g., utilizing finite-element calculation sheets or numerical methods computer programming).

The method 66 even further includes comparing the respective measured aperture positions for each of the expected aperture positions to the system specification of the CT imaging system for each expected aperture position (block 74). The system specification may be the respective dose tolerance threshold for each expected aperture position or an expected width for the expected aperture position. In certain embodiments, the comparison may be performed on the CT imaging system. In certain embodiments, the comparison may be performed separate or remote from the CT imaging system.

The method 66 still further includes generating an output based on the comparison of the respective measured collimator positions to the system specification for each of the expected aperture positions (block 76). In certain embodiments, generating the output includes generating a report that may be provided to the user/operator and/stored within the CT imaging system. In certain embodiments, generating the output includes generating a user perceptible notification (e.g., on a screen of a graphical user interface of a device of the CT imaging system or a device remote from the CT imaging system (e.g., computer, smart phone, etc.). In certain embodiments, the notification may include an alert that the pre-patient collimator needs to be replaced or soon will need to be replaced. In certain embodiments, the parameters (i.e., analysis of the aperture positions) may be monitored remotely (for connected CT imaging systems) for preventive maintenance of the collimator.

Figure 7:
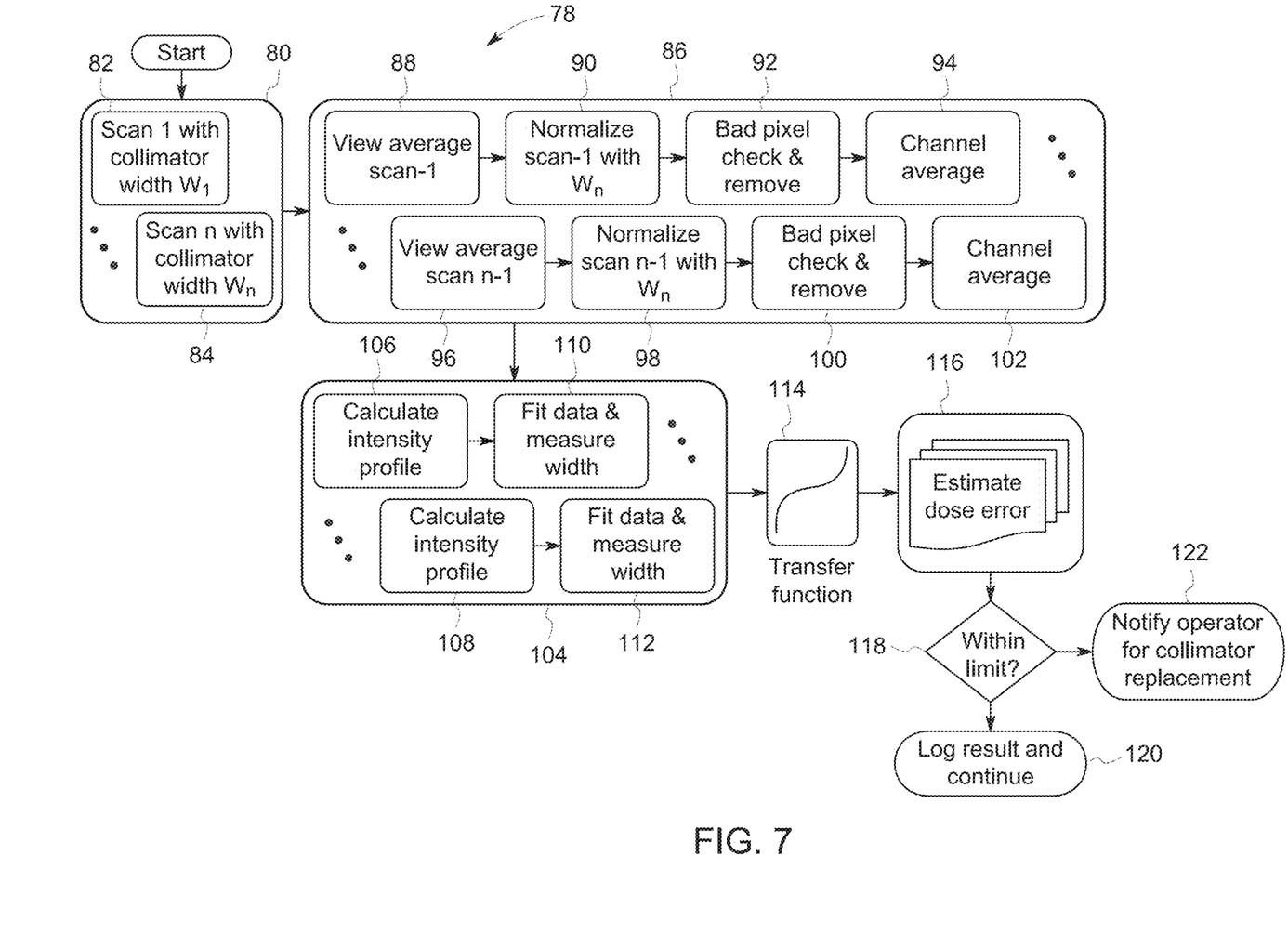
FIG. 7 is a block diagram a method for verifying aperture positions of a pre-patient collimator (e.g., of the CT imaging system in FIG. 1), in accordance with aspects of the present disclosure.

FIG. 7 is a block diagram a method 78 for verifying aperture positions of a pre-patient collimator (e.g., of the CT imaging system in FIG. 1). One or more steps of the method 78 may be performed by one or more components (e.g., processing circuitry) of the CT imaging system in FIG. 1. The method 70 includes initiating air scans (e.g., scans with no object within the bore of the gantry) on the CT imaging system at different expected (e.g., intended or predetermined) aperture positions or settings (e.g., 5 millimeters (mm), 10 mm, etc.) for the pre-patient collimator (block 80) as a standalone process or integrated within a refresh calibration scan process. As depicted, a number of scans may be conducted with a scan 82 (e.g., Scan 1) associated with the smallest aperture width ($W_1$) up to a scan 84 with the largest aperture width ($W_n$).

The method 78 also includes processing the obtained scan data at the different expected aperture positions (block 86). Processing includes normalizing the obtained scan data, removing bad pixel data, and obtaining a channel average. For example, an average of the scan data 88 obtained from the scan associated with the smallest aperture width ($W_1$) may be normalized with respect to the average scan data associated with the largest aperture width ($W_n$) as indicated by block 90. The normalized scan data associated with the smallest aperture width ($W_1$) may be checked for any bad pixels and the bad pixel data may be removed as indicated by block 92. Upon removing the bad pixel data, a channel average may be obtained for the normalized scan data associated with the smallest aperture width ($W_1$) as indicated by block 94.

Similar processing occurs for all of the obtained scan data at the different expected aperture positions (up to $W_{n-1}$ and excluding the scan data associated with the largest aperture width ($W_n$). For example, an average of the scan data 96 obtained from the scan associated with the aperture width $W_{n-1}$ may be normalized with respect to the average scan data associated with the largest aperture width ($W_n$) as indicated by block 98. The normalized scan data associated with the aperture width $W_{n-1}$ may be checked for any bad pixels and the bad pixel data may be removed as indicated by block 100. Upon removing the bad pixel data, a channel average may be obtained for the normalized scan data associated with the aperture width $W_{n-1}$ as indicated by block 102.

The method 78 includes further processing of the normalized obtained scan data (block 104). The further processing may include calculating a normalized intensity distribution profile for the normalized scan data associated with each expected aperture position. For example, calculating a normalized intensity distribution profile may occur on the normalized scan data that has been channel averaged (in block 94) associated with smallest aperture width ($W_1$) as indicated in block 106. Similarly, calculating a normalized intensity distribution profile may occur on the normalized scan data that has been channel averaged (in block 102) associated with the aperture width $W_{n-1}$ as indicated in block 108. A similar process may occur for all of normalized scan data associated with all of the aperture widths between $W_1$ and $W_{n-1}$. The width of the normalized intensity distribution profile is equivalent to actual measurement of the aperture or opening of the collimator (i.e., measured aperture position).

The further processing may also include fitting the data of normalized intensity distribution profiles (e.g., to a fitting function such as a Gaussian function) and then measuring a width of the measured normalized intensity distribution across the open aperture for each expected aperture position. For example, the normalized intensity distribution profile associated with the smallest aperture width ($W_1$) may be fitted and a width measured as indicated by block 110. Similarly, the normalized intensity distribution profile associated with the aperture width $W_{n-1}$ may be fitted and a width measured as indicated by block 112. A similar process may occur for all of normalized intensity distribution profiles associated with all of the aperture widths between $W_1$ and $W_{n-1}$.

The method 78 further includes converting the respective widths of the measured normalized intensity distributions for each expected aperture position to a respective dose utilizing a transfer function (block 114). The transfer function may be a linear transform function that changes the width or measured intensity value to the dose.

The method 78 even further includes determining a dose error estimate for each expected aperture position (block 116). Determining a dose error estimate may include comparing the doses derived from the widths of the normalized intensity distributions to the respective expected doses associated with each expected aperture position.

The method 78 still further includes comparing each respective dose error estimate to respective dose tolerance thresholds (e.g., dose tolerance range) for the different expected aperture positions (block 118). The comparison enables a determination to be made whether respective dose error estimates falls within or without (i.e., passes or fails) the respective dose tolerance threshold for each expected aperture position.

The method 78 yet further includes generating an output based on the comparison. For example, the method 78 includes logging or storing the result of the comparison in a memory within the CT imaging system or in a memory located in a remote location (block 120). As mentioned above, for connected CT imaging systems the logged information may be provided to a remote location for monitoring purposes for preventive maintenance of the collimator. The result or analysis may be logged or stored irrespective of the result (i.e., passing or failing). The method 78 also includes providing a user perceptible notification to a user/operator (block 122). For example, if one or more of the dose error estimates falls outside the respective dose tolerance thresholds, a notification may be provided that the pre-patient collimator needs replacement or will soon need replacement. The user perceptible notification may be provided on a screen of a graphical user interface of a device of the CT imaging system or a device remote from the CT imaging system (e.g., computer, smart phone, etc.).

Figure 8A:
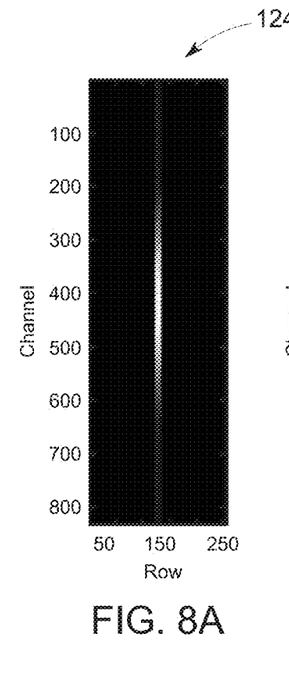
FIGS. 8A-8D are graphical representations of data during different stages of the verification of aperture positions of a pre-patient collimator, in accordance with aspects of the present disclosure.
Figure 8B:
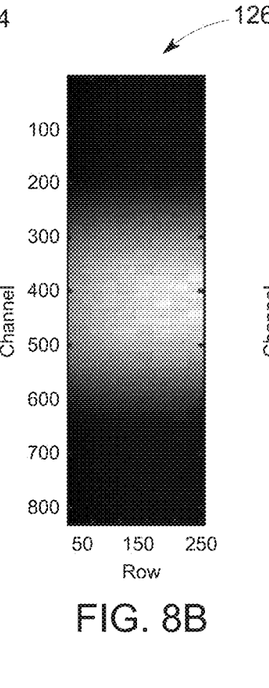
Figure 8C:
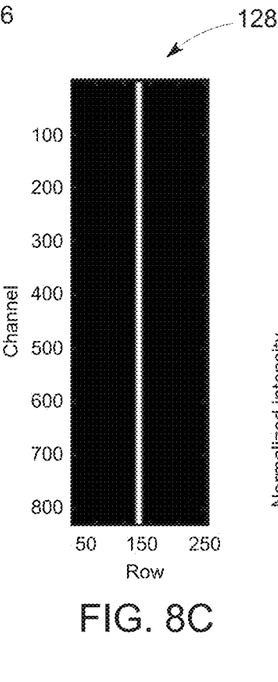
Figure 8D:
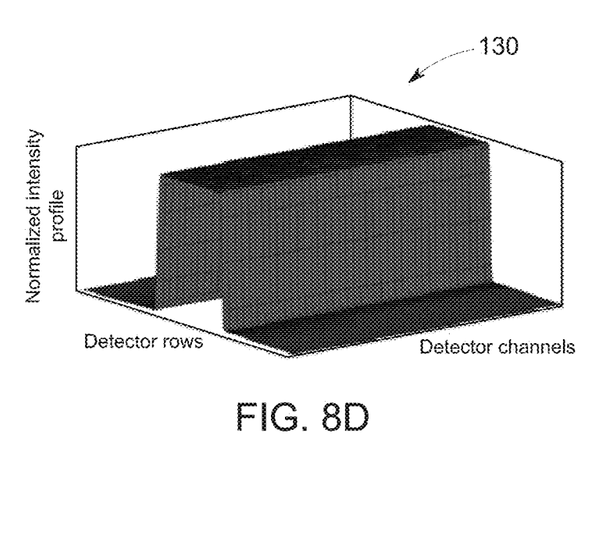

FIGS. 8A-8D are graphical representations of data during different stages of the verification of aperture positions of a pre-patient collimator. In particular, the graphical representations illustrate the obtained data at different stages of the data processing described in the method 78 of FIG. 7. FIG. 8A depicts a graphical representation 124 of view averaged scan data (e.g., of Scan 1 with $W_1$ as depicted in block 88 in FIG. 7). FIG. 8B depicts a graphical representation 126 of view averaged data (e.g., Scan n with $W_n$ as depicted in block 96 in FIG. 7). FIG. 8C depicts a graphical representation 128 of normalized scan data (e.g., normalized Scan 1 with $W_1$ as depicted in block 98). The normalized scan in FIG. 8C is derived by normalizing the view averaged data for Scan 1 with $W_1$ with respect to the view averaged data for Scan n with $W_n$ (e.g., as depicted in block 90 of FIG. 7). FIG. 8D depicts a graphical representation 130 of an intensity distribution profile of normalized data (e.g., as depicted in block 106 of FIG. 7). The intensity distribution profile in FIG. 8D may be data fitted (e.g., to a fitting function such as a Gaussian function) and a width of profile obtained from which a dose may be derived (e.g., via a transfer function).

Technical effects of the disclosed subject matter include providing systems and methods for performing collimator screening in a CT imaging system. In particular, the systems and methods enable the verification of aperture positions of a pre-patient collimator. The disclosed embodiments provide a safety check to ensure collimator blades are correctly positioned (e.g., regardless of collimator type or design). In addition, the disclosed embodiments may be utilized as a stand-alone tool or integrated with the daily refresh calibration process to enable the validation of the functionality of the collimator blades routinely. In certain embodiments, the parameters (i.e., analysis of the aperture positions) may be monitored remotely (for connected CT imaging systems) for preventive maintenance of the collimator. The routine monitoring of the collimator blade positions enables the preventive maintenance to be performed when required enabling the reduction in downtime for the CT imaging system. The disclosed embodiments provide a holistic approach combining system hardware and software for computation and analysis to corroborate the functionality of a critical hardware component (i.e., the pre-patient collimator) used in the CT imaging system to avoid providing an excessive radiation dose to a patient if the pre-patient collimator malfunctions (e.g., has an aperture opening larger than the expected aperture opening).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for verifying aperture positions of a pre-patient collimator of a computed tomography (CT) imaging system, comprising the acts of:
obtaining data collected by an X-ray measurement device having detector elements subjected to X-rays emitted from an X-ray source of the CT imaging system with the pre-patient collimator at an expected aperture position;
calculating a measured collimator aperture position for the pre-patient collimator based on the obtained data;
comparing the measured collimator aperture position to a system specification for the expected aperture position for the CT imaging system; and
generating an output based on the comparison of the measured collimator aperture position to the system specification.

2. The method of claim 1, wherein the X-ray measurement device is separate from the CT imaging system.

3. The method of claim 1, wherein the X-ray measurement device comprises a detector of the CT imaging system.

4. The method of claim 1, wherein the data comprises air scan data obtained during an air scan.

5. The method of claim 1, comprising:
obtaining the data collected by the X-ray measurement device having detector elements subjected to X-rays emitted from the X-ray source of the CT imaging system with the pre-patient collimator at a plurality of expected aperture positions;
calculating respective measured collimator aperture positions for the pre-patient collimator at the plurality of expected aperture positions based on the obtained data;
comparing the respective measured collimator aperture positions to the system specification for each expected aperture position of the plurality of expected aperture position for the CT imaging system; and
generating respective outputs based on the comparison of the respective measured collimator aperture position to the system specification.

6. The method of claim 1, wherein generating the output comprises storing a result of the comparison in a memory of the CT imaging system or a remote device.

7. The method of claim 1, wherein generating the output comprises providing a user perceptible notification of a result of the comparison.

8. A method for verifying aperture positions of a pre-patient collimator of a computed tomography (CT) imaging system comprising an X-ray source and a radiation detector, comprising the acts of:
acquiring air scan data by causing X-rays to be emitted from the X-ray source toward the radiation detector with the pre-patient collimator at different expected aperture positions;
calculating respective widths of respective normalized intensity distribution profiles for the pre-patient collimator at the different expected aperture positions based on the obtained air scan data;
converting the respective widths to respective doses utilizing a transfer function;
determining a respective dose error estimate at the different expected aperture positions based on the respective doses;
comparing the respective dose error estimates to respective dose tolerance thresholds for the different expected aperture positions; and
generating an output based on the comparison of the respective dose error estimates to the respective dose tolerance thresholds.

9. The method of claim 8, wherein calculating the respective widths comprises processing the obtained air scan data to calculate respective normalized intensity distribution profiles at the different expected aperture positions.

10. The method of claim 9, wherein processing the obtained air scan data comprises normalizing the obtained air scan data and removing bad pixel data prior to calculating the respective normalized intensity distribution profiles.

11. The method of claim 9, wherein calculating the respective widths comprises fitting the respective normalized intensity distribution profiles to a fitting function prior to calculating the respective widths.

12. The method of claim 8, wherein determining the respective dose error estimates comprises comparing the respective doses at the different expected aperture positions to respective expected doses at the different expected aperture positions.

13. The method of claim 8, wherein generating the output comprises storing a result of the comparison in a memory of the CT imaging system.

14. The method of claim 8, wherein generating the output comprises providing a user perceptible notification when one of the respective dose error estimates falls outside a dose tolerance threshold for a respective expected aperture position.

15. The method of claim 8, wherein the method is utilized as a standalone tool or during a daily calibration process.

16. A computed tomography (CT) imaging system, comprising:
- an X-ray source configured to emit X-rays during operation;
- a radiation detector configured to receive the X-rays;
- a pre-patient collimator disposed between the X-ray source and the radiation detector and configured to shape a beam of the X-rays via an aperture; and
- processing circuitry configured to perform acts comprising:
  - acquiring air scan data by causing X-rays to be emitted from the X-ray source toward the radiation detector with the pre-patient collimator at different expected aperture positions;
  - calculating respective widths of respective normalized intensity distribution profiles for the pre-patient collimator at the different expected aperture positions based on the obtained air scan data;
  - converting the respective widths to respective doses utilizing a transfer function;
  - determining a respective dose error estimate at the different expected aperture positions based on the respective doses;
  - comparing the respective dose error estimates to respective dose tolerance thresholds for the different expected aperture positions; and
  - generating an output based on the comparison of the respective dose error estimates to the respective dose tolerance thresholds.

17. The CT imaging system of claim 16, wherein calculating the respective widths comprises processing the obtained air scan data to calculate respective normalized intensity distribution profiles at the different expected aperture positions.

18. The CT imaging system of claim 17, wherein processing the obtained air scan data comprises normalizing the obtained air scan data and removing bad pixel data prior to calculating the respective normalized intensity distribution profiles.

19. The CT imaging system of claim 16, wherein determining the respective dose error estimates comprises comparing the respective doses at the different expected aperture positions to respective expected doses at the different expected aperture positions.

20. The CT imaging system of claim 16, wherein generating the output comprises providing a user perceptible notification when one of the respective dose error estimates falls outside a dose tolerance threshold for a respective expected aperture position.

* * * * *